United States Patent
Stern et al.

(10) Patent No.: US 7,904,824 B2
(45) Date of Patent: Mar. 8, 2011

(54) MEDICAL IMAGING PROGRAMMABLE CUSTOM USER INTERFACE SYSTEM AND METHOD

(75) Inventors: Steven J. Stern, Issaquah, WA (US); Levin F. Nock, Bellevue, WA (US); Laurence S. McCabe, Sunnyvale, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 873 days.

(21) Appl. No.: 10/315,469

(22) Filed: Dec. 10, 2002

(65) Prior Publication Data

US 2004/0109028 A1 Jun. 10, 2004

(51) Int. Cl.
*G06F 3/00* (2006.01)

(52) U.S. Cl. .......................... 715/771; 715/765

(58) Field of Classification Search ................. 715/771, 715/744

See application file for complete search history.

(56) References Cited

U.S. PATENT DOCUMENTS

| | | | | |
|---|---|---|---|---|
| 5,161,535 A * | 11/1992 | Short et al. | ..... | 600/437 |
| 5,315,999 A * | 5/1994 | Kinicki et al. | ..... | 600/443 |
| 5,715,823 A * | 2/1998 | Wood et al. | ..... | 600/437 |
| 5,739,451 A * | 4/1998 | Winksy et al. | ..... | 84/609 |
| 5,754,174 A * | 5/1998 | Carpenter et al. | ..... | 715/810 |
| 6,063,030 A * | 5/2000 | Vara et al. | ..... | 600/437 |
| 6,229,539 B1 * | 5/2001 | Morcos et al. | ..... | 715/808 |
| 6,306,089 B1 * | 10/2001 | Coleman et al. | ..... | 600/437 |
| 6,411,836 B1 * | 6/2002 | Patel et al. | ..... | 600/407 |
| 6,480,186 B1 | 11/2002 | McCabe et al. | | |
| 6,599,244 B1 | 7/2003 | Epps et al. | | |
| 6,771,290 B1 * | 8/2004 | Hoyle | ..... | 715/745 |
| 6,799,135 B2 * | 9/2004 | Sone | ..... | 702/127 |
| 2001/0004310 A1 * | 6/2001 | Kono | ..... | 361/683 |
| 2002/0077862 A1 * | 6/2002 | Auer et al. | ..... | 705/3 |
| 2002/0138512 A1 * | 9/2002 | Buresh et al. | ..... | 707/507 |
| 2002/0167549 A1 * | 11/2002 | Cupples et al. | ..... | 345/835 |
| 2004/0061630 A1 * | 4/2004 | Rose | ..... | 341/22 |

\* cited by examiner

*Primary Examiner* — Ryan F Pitaro

(57) ABSTRACT

Methods and systems for a user to create a custom menu for medical imaging are provided. To maximize the ease of use and increase user efficiency, the user interface is tailored to a particular user or for a certain application. The user selects from various imaging parameters in a preprogrammed user interface displayed on a monitor or other display device. The selection is by collecting the desired items or by discarding undesired items. After selection, the desired items are displayed in a customized display state. This customized display state can be labeled and stored for later use. An assignable key is also provided. Imaging functions, such as a type of B-mode or Doppler imaging, are assigned to the key. Different or new functions may be later assigned to the key as the most used imaging functions change. Any customization may be different for different users of the same system, such as by saving the customization related to a log-on procedure.

17 Claims, 2 Drawing Sheets

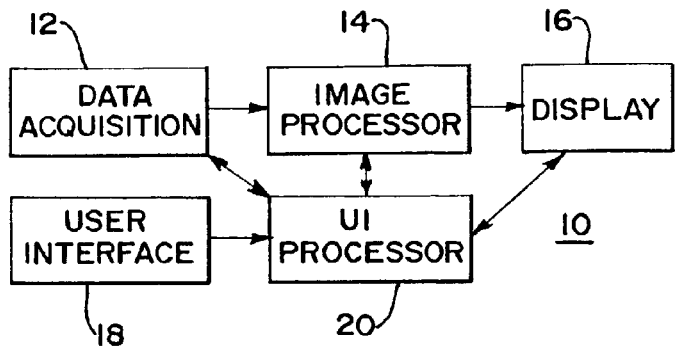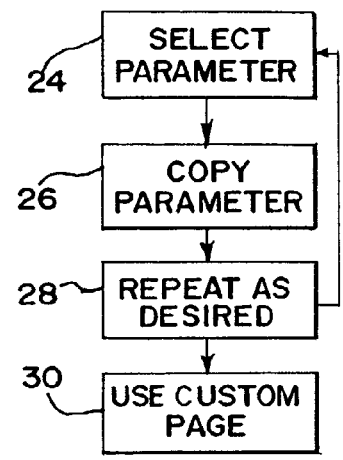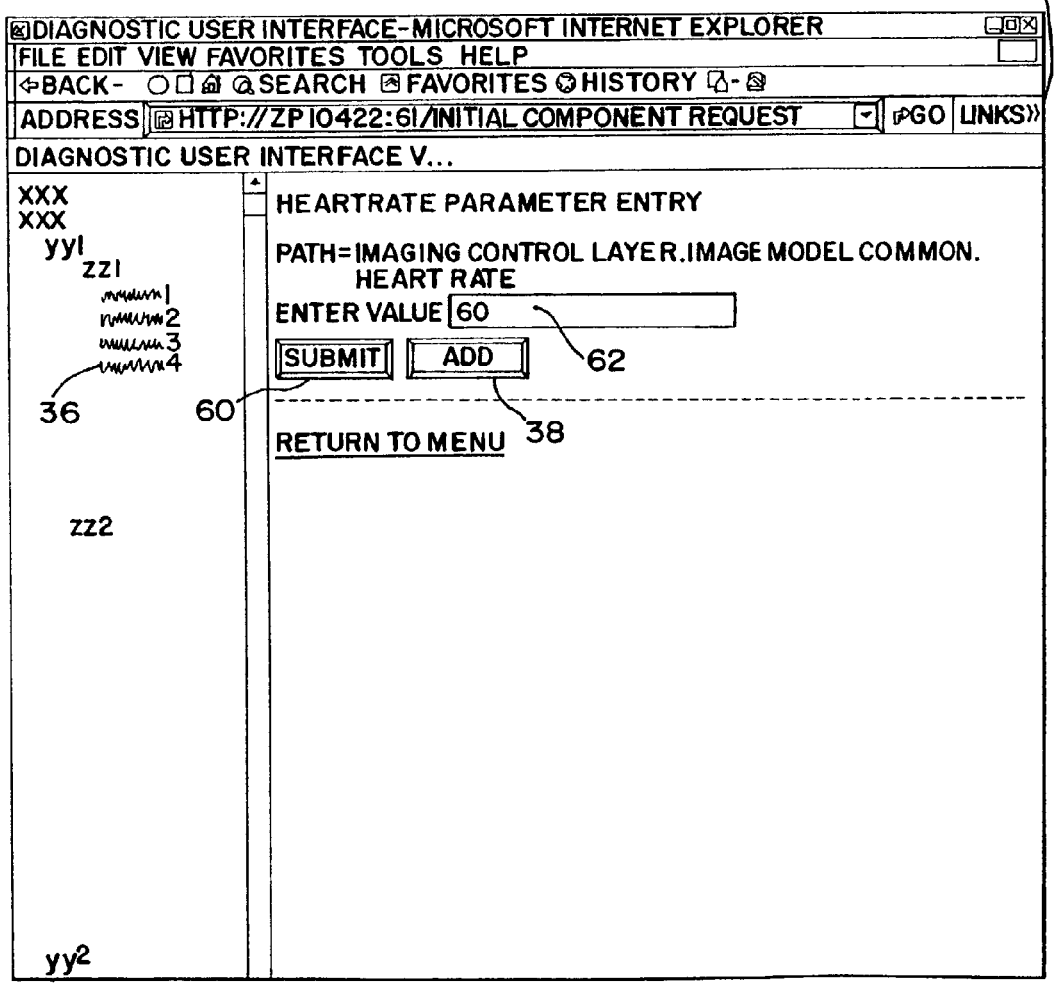

MEDICAL IMAGING PROGRAMMABLE CUSTOM USER INTERFACE SYSTEM AND METHOD

BACKGROUND

The present invention relates to programmable user interface for medical imaging system. In particular, the user interface is customized by a user or other operator of an imaging system.

Medical imaging devices, such as ultrasound, magnetic resonance, computed tomography, or other medical diagnostic imaging systems have increasing complexity and functionality. In order for one system to cover a broad range of applications with optimal performance, a user interface typically includes a large number of inputs and outputs. For example, a complex menu structure grouping various imaging parameters on different menus or pages is provided. Since some users specialize in particular imaging applications, only a, small subset of the imaging parameters provided on the user interface may be used. Currently available menu structures provide factory or preprogrammed sets of menus associated with multiple applications. For dealing with multiple imaging parameters, a user may have to navigate between different pages or sets of the menu system. For example, a debug user interface may require the user to monitor several parameters located in different parameter containers or on different menu pages. The user is then required to flip between these multiple menu pages or parameter containers, resulting in inefficient debugging of the imaging system. Where several discrete parameters are located on different pages but are all monitored or modified for a same medical diagnosis, inefficient navigation of the menu structure results.

Some customization may be available to the user. For example, user defined presets of particular imaging parameter values may be created and saved. VCR controls, user defined icons or other toolbar controls may be dragged or positioned to other toolbar locations. As another example, ultrasound systems may include touch screens allowing a user to control a particular calculation displayed on the touch screen. However, these limited examples of adaptability may still result in the user navigating between various pages or menu structures. Furthermore, the user may be presented with information and choices in which they have no interest, distracting them from the task at hand.

BRIEF SUMMARY

The present invention is defined by the following claims and any claims subsequently added based on the disclosure herein, and nothing in this section should be taken as a limitation on those claims. By way of introduction, the preferred embodiments described below include methods and systems for a user to customize the user interface for medical imaging. To maximize the ease of use and increase user efficiency, the user interface is tailored to a particular user or for a custom application. For example, the user selects from various imaging parameters or objects in a preprogrammed user interface displayed on a monitor or other display device. The desired items are collected or undesired items are discarded. After selection, the desired items are displayed in a customized display state. This customized display state can be labeled and stored for later use.

In one aspect, different imaging parameters are selected from different preprogrammed menus. The selected imaging parameters are then provided on a custom interface for efficient access.

In a second aspect, a custom page is provided as part of a menu that also includes a plurality of objects, such as imaging parameters or display objects. The user selects with a user interface at least one of the objects. The selected object is provided on the custom page.

In a third aspect, one of multiple imaging functions is selected by a user. A key on a keyboard is assigned to the selected imaging function. The selected imaging function is then activated in response to operation of the assigned key.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a medical diagnostic imaging system.

FIG. 2 is a flow chart diagram of one embodiment for customizing a user interface.

FIG. 3 is one embodiment of a preprogrammed menu page including an imaging parameter.

DETAILED DESCRIPTION OF THE PREFERRED EMBODIMENTS

Figure 4:
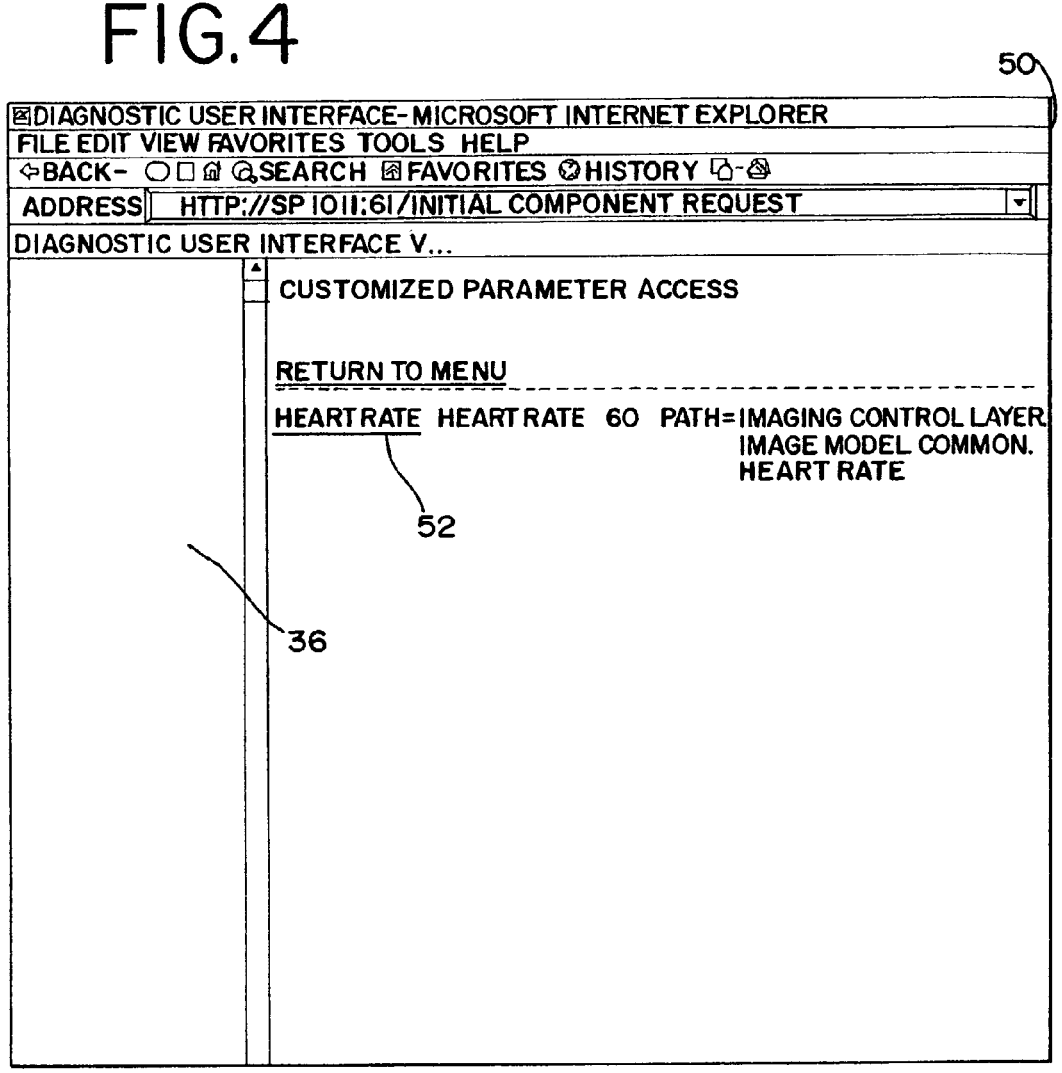
FIG. 4 is a graphic representation of a customized page having one selected imaging parameter.

Providing a custom page within a menu structure for an imaging system may increase examination throughput. Parameters from preprogrammed or other existing menus are copied, moved or selected for inclusion on a customized page. By enabling placement of personal preferenced objects on a single page, a debugger, scanning technician, medical professional or other user creates a personal preference page of imaging parameters or other objects. The user can change modifiable objects, add additional objects, or delete objects from the custom page for versatile customization and to reflect changes to the needs of the user over time. The customized page avoids the use of submenus and switching between different pages for different service routines, or medical applications. Different examination preferences, imaging parameters, measurement preferences, system controls, post-processing parameters, signal processing, data storage, system configuration or other objects of the imaging system are easily customized.

In one embodiment, software-based customization using the above described custom page or other menu structure is implemented by the medical imaging system. In another embodiment, the software interacts with a key of a keyboard or control panel (i.e., hard key) to assign one of various possible imaging functions to the key. Other customizations using one or more of various aspects of one or both of the two above described embodiments may be used.

FIG. 1 shows a medical imaging system 10 for a user to create a custom menu. The system 10 includes a data acquisition device 12, and image processor 14, a display 16, a user input 18, and a user interface processor 20. Additional, different or fewer components may be provided. The system 10 comprises one of various medical imaging devices, such as a magnetic resonance imaging system, computed axial tomography system, an ultrasound imaging system, or other medical diagnostic imaging system now known or later developed.

The data acquisition device 12 is one of various hardware, software and other structures for acquiring medical imaging data. For example, in a medical diagnostic ultrasound system, the data acquisition device 12 comprises an ultrasound transducer for transducing between acoustic and electrical energies to scan a patient. The image processor 14 comprises one or more of a digital signal processor, a general processor, application specific integrated circuit, filter, memory, scan converter, detector, analog device, digital device or combinations thereof. For example, the image processor 14 comprises transmit and receive beamformers, B-mode and/or Doppler detectors, scan converter and one or more filters of an ultrasound imaging system.

The user input 18 comprises one or more input devices, such as one or more of a keyboard, mouse, scroll wheel, track ball, joy stick, touch screen, dedicated hard keys, slides, switches, knobs, radio buttons, soft buttons (software controlled buttons), position sensing devices, rocker switches, slider or other now known or later developed user input devices. In one embodiment, the user input 18 is on a keyboard of the medical imaging system, but may be positioned on a peripheral device connected directly or indirectly to the system, such as a remote input device. The user input 18 allows a user to input information into the system 10, such as for debugging or scanning a patient.

The display 16 comprises a monitor, CRT, LCD, plasma screen, viewfinder, flat panel, projection or other display device now known or later developed for displaying a medical image, such as an ultrasound B-mode or color Doppler image. In conjunction with the user interface processor 20 and the user input 18, the display 16 is operable to display various menus, a custom page, a custom menu and/or preprogrammed menus as a user interface.

The user interface processor 20 comprises general processor, a digital signal processor, an application specific integrated circuit, analog device, digital device and/or combinations thereof. The user interface processor 20 may be physically implemented as an integral part of the user input 18 or the image processor 14 rather than a distinct processor. Other now known or later developed processors may be used. The interface processor 20 interacts between the user input 18, the image processor 14 and/or the display 16. For example, the user interface processor 20 controls operation of the image processor 14 with one or more imaging parameters for generating an ultrasound or other medical image. The control of the imaging processor 14 and the system 10 is implemented through the interaction of the user input 18 and user selections based on information on the display 16. In one embodiment, software on the user interface processor 20 provides tools for copying or otherwise indicating imaging parameters or objects for use on a custom menu or a custom page in response to a user selection. For example, the user selects one or more imaging parameters from different preprogrammed menus for providing the selected imaging parameters on a single custom page or as part of a custom menu setup.

The user interface processor 20 operates pursuant to software in any of various now known or later developed programming language. For example, HTML or XML files, objects and/or scripts are provided in any of various menu structures. Custom programmed menu structures and associated display software may be used in alternative embodiments.

FIG. 2 shows a flow chart of one method for creating a custom menu or custom page in medical imaging. The method is implemented by the user interface processor 20 or other processor.

At least one menu is provided for display to the user. The preprogrammed menu provided to the user includes parameter containers or pages in any of various structures, such as single layer, multiple layer, tree, tunneled, or other menu structures. For example, the menu is divided into various application oriented pages or groupings of imaging parameters. One preprogrammed page or menu is different than another preprogrammed page or menu. For example, an entirely different, partially different or subset of imaging parameters or objects is provided in one page as compared to another page. Any given page or menu structure may include one, two or more, such as hundreds of objects or imaging parameters. For example, a preprogrammed page provides real time control imaging parameters, such as vector tables and scan sequencing information. As another example, a preprogrammed page includes imaging parameters associated with frame rate for controlling higher level sequencing, such as triggering, calculation and other timing information. As yet another example, a contrast state preprogram page is provided with imaging parameters associated with contrast agent imaging. Pages associated with B-mode scanning, Doppler scanning, three-dimensional imaging, two-dimensional imaging, transducer type, waveform generation or other imaging functions or applications are possible. Other menu structures with different groupings of imaging parameters and parameter objects may be provided.

As used herein, imaging parameter includes any of various variables or tables of variables for controlling the acquisition, data storage and image processing of medical image information. Imaging options include imaging parameters available to a user for setting or enabling. For ultrasound applications, imaging parameters include beam forming variables, filter variables, B-mode detection variables, Doppler detection variables, spectral Doppler detection variables, scan converting variables, post-processing parameters, signal processing, data storage, system configuration and any other now known or later developed variables associated with generating an ultrasound image. For example, imaging parameters include the user controlling the storage of data from one of multiple locations along the processing path for later generation of an image, configuring the system to collect data on an element-by-element basis or running a specific script for imaging. Beamforming parameters include scan line spacing, angle, origin, signal frequency, pulse repetition frequency, sampling rate, or other now known or later developed beamforming variables. Filtering parameters include weights, number of taps, infinite impulse response characteristic, finite impulse response characteristic, pass band, or other now known or later developed filtering characteristic. Objects include imaging parameters as well as non-imaging parameters, such as values calculated from imaging information, information for interfacing with other systems, such as VCRs, memories, network transmission, display objects for annotation, display format, and graphics, or other now known or later developed variables used by the system 10. A page includes a window, box, section of a screen, an entire screen or other collection of display information. In an alternative embodiment, a menu, outline, icons, tool bar or other organization of objects is provided.

In act 24 of FIG. 2, the user selects one or more imaging parameters or objects with the user input 18. For example, a heart rate imaging parameter is selected from a imaging control page with a plurality of different imaging parameters in a list. As shown in FIG. 3, a preprogrammed page for a single heart rate imaging parameter is provided. The preprogrammed page 34 is selected from one of a plurality of groupings of imaging parameters in a menu structure summarized in a hierarchy at 36 (e.g., the imaging control page). The selection is performed by double clicking or highlighting and depressing the enter button in a Microsoft windows or Internet Explorer format. Other user interface software and formats may be provided. To further select the imaging parameter for use on a custom page, the user selects an add button 38. The add button 38 is implemented through software, but may alternatively be implemented as a hard key. The selection of act 24 is implemented in one embodiment as a shopping cart type function. A customized or add to customization page button is provided for each discrete parameter either on a separate page for each parameter or as part of a menu listing of multiple parameters on a same page. In other embodiments, other tools for selecting an object may be provided, such as clicking and dragging, highlighting, selecting with an unique input, using a combination of keystrokes on a keyboard, software button, dedicated hardware button, deselection from a preprogrammed list or other now known or later developed selection processes.

In act 26, the selected parameters are copied or provided on the custom page 50 as shown in FIG. 4. The parameter and associated information 52 is provided as part of a list of one or more selected parameters on the custom page. The parameter 52 is linked to software associated with the parameter, such as by an XML object script. The custom page 50 comprises a page within the menu hierarchy 36 or as part of a separate menu. The custom page includes a window, an entire screen, a section of a screen, or other grouping associated with a user adapted selection of multiple imaging parameters or parameter objects. In one embodiment, the custom page 50 comprises a single page, but multiple custom pages may be provided. In alternative embodiments, a combination of pages, a toolbar, an icon, a menu structure, a portion of a preprogrammed page, or other grouping of information is provided for listing the selected objects in a custom grouping. The custom page is preprogrammed to exist as a blank page until filled by the user selection in act 24 or includes a plurality of imaging parameters and objects that may be maintained or removed as part of the customization.

In act 28, the selection and copying of the objects is repeated as desired. For example, the user selects one, two or more of the various imaging parameters from one or more menus or other groupings of imaging parameters. The act 28 of repeating the selection and copying of parameters is optional. For example, a user may generate a custom page with a single object or only deselect a single object.

After each object is copied, or after all of the objects are copied, the custom page 50 is displayed on the display 16. For example, the user interface processor 20 causes the custom page 50 to automatically display after a new object is selected. Alternatively, the custom page 50 is displayed in response to a user selecting the custom page 50 for display. The displayed custom page 50 includes imaging parameters or other objects. The list of one or more objects is different on the custom page 50 than any other grouping of objects provided in the preprogrammed menu. In alternative embodiments, the custom page 50 includes the same set of parameters or objects as another preprogrammed page. For example, a user may want to associate a particular page with a different name, such as the user's name, for ease of access or provide different presets to the same imaging parameters.

The custom page 50 is stored for later use. For example, the XML, HTML or other links or object lists or tables defining the parameters placed on the custom page are stored in a memory within the system 10. A user name or other reference information is used to reference the custom page 50. Multiple different custom pages 50 or custom menus may be created and stored. For example, different custom pages 50 correspond to different users or user names. In one embodiment, one or more custom pages 50 are accessed as part of a login procedure. For example, a particular user logs into the system 10. Based on the login identification, one or more custom pages 50 are made available as part of the menu structure or hierarchy 36 for that user. Alternatively, all of the previously created custom pages 50 are available to a user. The user selects the desired custom page 50 for use.

The custom page 50 is used in act 30 in various environments. For example, a technician attempting to debug software or other problems with the system 10 creates a custom page 50 of imaging parameters or other objects of interest for debugging. Rather than flipping back and forth between different pages, menus or containers, the objects to be used for debugging are provided on a single page or within a single menu structure. Customizing the interface allows for convenient setting of examination preferences, measurement preferences, system controls and other objects for determining where an error or undesired performance is occurring.

For debugging or other uses, one or more of the imaging parameters or objects may be modified. For example, the user selects an imaging parameter 52 from the custom page 50 as shown in FIG. 4. The imaging parameter page 34 includes a box 62 or other area for indicating a change of a variable corresponding to the imaging parameter. After setting the imaging parameter to a desired value, the imaging parameter is saved or confirmed, such as by submitting the parameter value by clicking on the submit button 60. Alternatively, depressing the enter button or another user input sets the imaging parameter to the desired variable value or otherwise saves the variable. Modifiable objects allow for saving or presetting the parameters or objects. In one embodiment, objects are saved or preset for use with the custom page differently than for uses with other pages, but may be saved or preset for all pages or uses within the menu. In an alternative embodiment, a location to enter changes for each object is provided as part of the list on the custom page 50, avoiding or minimizing having to bring up a different page to make changes. In the debugging example discussed above, the user changes one or more imaging parameters or objects to view any resulting changes in other parameters or objects either prior to, during or after examination. The parameters or object changes are shown on the custom page 50 or object specific pages easily accessed from the custom page. The technician then makes further changes to the system based on identified problems.

In one embodiment, the selection of parameters or objects for use on the custom page 50 alters the output of the display during imaging, such that information associated with the parameters or objects is displayed and unselected objects or parameters are not displayed or displayed according to a user defined or predefined priority function. Alternatively or additionally, the object variables are accessed through the custom page 50.

As another example use, a medical technician in a clinical environment creates one or more custom pages 50 or other menus. Different customized pages 50 correspond to different clinical applications or examinations, such as uncommon examinations using different groupings of imaging parameters or objects. To avoid flipping between different pages and different menus, the custom page 50 allows the clinical technician to review, modify or use different imaging parameters and objects from a single page or from a single menu before, during or after an examination.

As yet another example of use, a medical diagnosis imaging professional creates and uses a custom page 50 of imaging parameters and/or other objects. While a standard or preprogrammed menu and pages of parameters and objects are more likely adapted for typical medical imaging in a diagnostic environment, a user may prefer a custom configuration of objects for a particular diagnostic use. In either the clinical or the medical diagnostic environments, the system 10 is used to image or generate medical images in response the imaging parameters on the custom page 50. Changes to the imaging parameters affect the resulting images. Information calculated, collected or displayed in response to the objects is provided to the user on the custom page or on a display during imaging in response to inclusion on the custom page 50.

In one embodiment, the image on the display 16 while displaying a medical diagnostic image is responsive to the selection of parameters and objects from the custom page 50. Examination is initiated using the custom page 50 or with variable settings based on the custom page 50. The information output on or adjacent to the image, such as display objects (e.g. calculations) or imaging parameters included on the custom page 50 are displayed. In response to inclusion on the custom page 50, the display is updated to add the included information or to replace information not included. For example, each object corresponds to an XML object. The script of the XML statements is run to create graphics on the display based on inclusion in the custom menu. By allowing the user to control the displayed information, information irrelevant to a user may be removed or maintained on the display. Where irrelevant information is removed, the desired information associated with the custom menu is displayed and may be displayed in a larger size. In one embodiment, the user selects the position of the display of any object, but the software of the user interface processor 20 may automatically configure the display or organization of the display.

In one embodiment, the custom page is configured as a display screen with an image. Each addition of an object is added to the representative display screen. The user may move the selected objects within the representative display screen to different positions to configure the display for real time or post examination viewing of an image.

In alternative embodiments, the information displayed with an image is maintained regardless of the selected objects on the custom menu. To review information associated with the custom menu, the user selects the custom menu for display. The custom menu may be displayed alongside the image window or display, such as in a split screen or as multiple overlapping windows on the display 16. The custom menu allows the user to either configure the system 10 for scanning or configure the output on the display 16 or combinations thereof.

Different user interfaces may be provided for the different types of users, such as providing a separate debugging and clinical or medical diagnostic user interfaces. The same or different customization pages or menus may be provided in any of the various user interface configurations.

The user creates and uses the custom page locally at the system 10. In an additional or alternative embodiment, the system 10 connects with a remote work station or another remote system 10. For example, an intranet, Internet, modem, wireless, combinations thereof, or other now known or later developed communications connections are provided from the system 10 to a remote work station. A user at the remote work station controls the graphic user interface of the system 10 and/or controls the system 10. The user at the remote work station can create and use a custom page 50. For example, a technician at the manufacturer can debug using a custom menu in systems 10 at various locations without requiring travel. In other embodiments, a custom page 50, custom menu, custom output display or other information is exported from the system 10 to a remote display device. Control from the remote work station may be minimized or not provided, but information from the system 10 is exported for viewing and analysis by remote users.

In another embodiment, the user customizes the user interface by altering a list of user options. The user options include imaging parameters, objects or a menu structure. For example, the list or the menu structure 36 includes a plurality of options, such as selectable pages of imaging parameters. In response to user input, the list of pages on the menu structure 36 is, altered, such as increasing or decreasing the number of user options. Where a user is likely to use a lesser number of menu pages, the menu structure 36 is altered to display the appropriate menu pages in response to user identification of the desired options (e.g. deleting undesired options or selecting the desired options). For example, where a user rarely alters the frequency of operation of the system, an option for selecting a list of imaging parameters associated with the frequency of operation is removed from the list in response to user input. By removing menu page options from the list, the list is more compact and desired options may be displayed more prominently (e.g. with a larger font). In another example, a preprogrammed menu structure 36 lacks an option frequently used by a user, so the option is added to the menu structure 36 in response to user selection of the addition. The altered list is then displayed for use by the user. A custom page of objects may or may not be included in the list of options.

In one embodiment, the customized list of options is responsive to user identification. A saved custom list is used one or more times after creation. For example, a log-on procedure with user identification is provided. In response to a user logging onto the system, any custom list associated with the user is displayed rather than the preprogrammed list in response to the user identification. The customized list may also or alternatively vary as a function of imaging application. For example, a user selection of a particular imaging application results in display of a customized list associated with that imaging application. For a different imaging application, a different preprogrammed or customized list of options is displayed.

Figure 5:
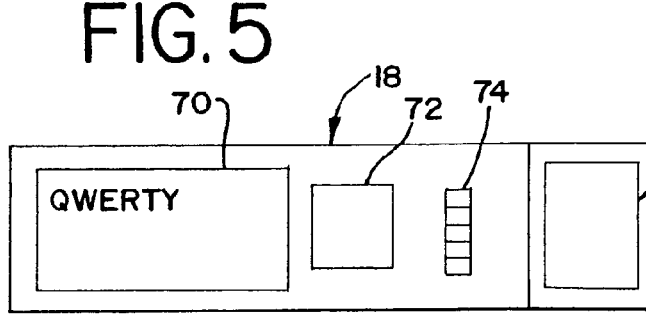
FIG. 5 is a block diagram representation of one embodiment of a user input.

FIG. 5 shows a system for user customization of keyboard functions. The user input 18 (i.e. control panel) includes a QWERTY keyboard 70, a mouse or track ball input 72 and one or more additional hard keys 74. Additional, different or fewer inputs may be provided on the user interface 18, such as a touch screen 76 or now known or later developed user interfaces used in any of the various imaging systems discussed herein. The hard keys 74 comprise keys on a keyboard of the user input 18. The keys 74 are included as part of the QWERTY keyboard 70 or as separate keys on part of the overall keyboard of the user input 18. The hard keys 74 comprises push button, toggle, rocker, slides or other physically set switches or input devices. In alternative embodiments, the keys 74 include an LCD display, touch screen, touch sensor or other input device on the keyboard of the user input 18. The user input 18 may be contiguous in space as shown, or may consist of input devices at multiple locations. For example, a QWERTY keyboard 70 at one location, hard keys 74 in another location and more hard keys in a third spaced apart location.

In addition to the hard keys 74, dedicated hard keys may be provided on the user input 18 for implementing various imaging functions. Often, new imaging functions implemented by the system 10 may not include a dedicated key.

The user of input 18 is connected with the remainder of the system 10 and the display 16 as shown in FIG. 1. The display 16 is operable to display a menu with at least two imaging functions. For example, the software of the user interface processor 20 provides a list of any number of imaging functions, such as six or more. Imaging functions include any of various now known or later developed imaging applications. For example, imaging functions include standard B-mode imaging, Doppler velocity imaging, Doppler energy imaging, three-dimensional imaging, contrast agent imaging, triggered imaging, image compounding, image filter or other imaging, scanning or processing function that may start an examination, or change during an examination. The displayed list of imaging functions includes only imaging functions without dedicated keys for implementation, only imaging functions with dedicated keys or combinations of functions with and without dedicated keys. Imaging functions not organized as a single list may also be selected for assignment to a hard key 74.

In response to input 18 by the user, the user interface processor 20 is operable to assign one of the imaging functions from the list to one of the hard keys 74. Any of new or old imaging features from the list is assigned to a particular hard key 74. The imaging function is initiated in response to operation of the hard key 74. Where an imaging function is no longer likely to be used or has reduced importance, a different imaging function may be later assigned to the same hard key 74.

In one embodiment, only one hard key 74 is provided, but in alternative embodiments, two or more (e.g. three) customizable hard keys 74 are provided on the user interface 18. Different listed imaging functions are assigned to different of the customizable hard keys 74. Software of the user interface processor 20 links the selected imaging function to the assigned key 74 in a table or other memory. When the user depresses the key 74, the user interface processor receives an indication that key 74 is depressed and initiates the imaging function.

In one embodiment, a key designator, such as a removable key cap, is provided for each imaging function. For example, a software update of the medical imaging system 10 includes two new imaging functions, such as an imaging function for contrast agent imaging of a particular contrast agent and a harmonic imaging function including second and third harmonic information in the image. The software upgrade automatically updates the list of imaging functions provided to the user for assignment to hard keys 74. Provided with the software update are two removable key caps, one key cap for each of the additional imaging functions. If the user assigns a hard key 74 to a particular imaging function, the removable key cap with a label for the selected function is placed over the key 74. In alternative embodiments, the key designator comprises removable label, LCD, LED, software based labeling, touch screen or no label is provided on an assigned key 74. When the key 74 is assigned to a different imaging function, the removable key cap is removed from the key 74 and a new removable key cap may be placed over the key 74.

Figure 6:
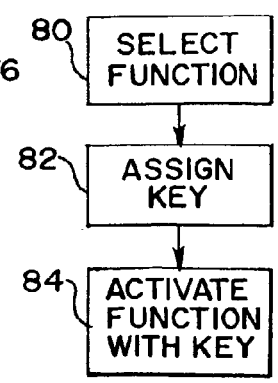
FIG. 6 is a flow chart of one embodiment of a system for customizing an assignable key.

FIG. 6 shows a method for customizing a keyboard for medical imaging. As discussed above, at least two imaging functions are listed on a feature list provided to the user. The list is displayed on the display 16 or provided in written material. In alternative embodiments, individual imaging functions separate from any list or part of a sub list are provided to the user.

In act 80, the user selects an imaging function. For example, the user highlights, clicks, drags or otherwise indicates an imaging function from a list. As another example, the user inputs a code, selects an imaging function from a menu hierarchy, or otherwise indicates an imaging function for selection.

In act 82, one of the keys 74 on the keyboard of the user input 18 is assigned to the selected imaging function. For example, the user depresses the key 74 after highlighting or otherwise selecting the imaging function. In an alternative embodiment, a software representation of the available keys is provided and the user matches the selected imaging function with the software representation of the key, such as by double-clicking after selecting the imaging function, clicking and dragging the imaging function to the representation of the key or other now known or later developed software or hardware based mechanisms for linking an imaging function with the key 74. The selection and assigning acts 80 and 82 are performed for a single key 74 or may be repeated for additional keys and imaging functions.

In act 84, an imaging function is activated by depressing the assigned key 74. For example, the user depresses the key 74 assigned to a particular type of harmonic imaging during an examination. Subsequent images are generated in response to the assigned harmonic imaging function. As another example, a particular type of Doppler imaging is activated as an overlay on a B-mode image in response to activation of the imaging function by depressing the key 74. As yet another example, imaging is initiated by depressing the key 74 associated with an imaging function. Additionally or alternatively, an imaging function is deactivated or discontinued in response to activation of the assigned key 74.

In one embodiment, the assignment of one or more of the hard keys 74 is different for different users. For example, one grouping of imaging functions with hard keys 74 is provided for one user in response to that user inputting identifying information (e.g. logging on). A different grouping is provided for a different user.

While the invention has been described above by reference to various embodiments, it should be understood that many changes and modifications can be made without departing from the scope of the invention. For example, a software based customized menu or page may be used with or without the user assignable key embodiments and vice versa. Any number of software or hardware based mechanisms for selecting, activating, assigning, copying or providing may be used. While many of the various examples discussed above are for ultrasound medical diagnostic imaging or the generation of images from ultrasound information, other medical imaging devices may use the customizable user interfaces discussed herein.

It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. A method for creating custom access in a medical imaging system comprising:
   (a) displaying a preprogrammed, existing menu of one or more unmapped imaging options available to a user, the existing menu including the unmapped imaging options in a standard menu for controlling the medical imaging system as part of an existing user interface;
   (b) selecting, with a user interface of the medical imaging system operable with a data acquisition device for scanning a patient, the one or more unmapped imaging options from the displayed preprogrammed menu; and (c) mapping selected ones of the unmapped imaging options from the displayed preprogrammed menu for custom access on a custom page of the imaging options, where the mapped imaging options are used by the data acquisition device for scanning the patient, the mapping comprising creating a display of user selectable options corresponding to the mapped imaging options on the custom page, the custom page being for controlling the data acquisition device and being different than any of the preprogrammed, existing menus including the displayed preprogrammed, existing menu.

2. The method of claim 1 wherein the custom access comprises one or more soft controls including at least one of menus, radio buttons, soft buttons, and sliders; and wherein the user interface is disposed on one of: the medical imaging system keyboard, and a peripheral device connected to the medical imaging system.

3. The method of claim 1 wherein the imaging options include one or more of: imaging parameters, post-processing parameters, signal processing, data storage, system configuration and imaging functions.

4. The method of claim 1 wherein (b) comprises selecting with the user interface first and second imaging parameters from respective first and second preprogrammed menus, the first preprogrammed menu different than the second preprogrammed menu; and wherein (c) comprises providing the first and second imaging parameters on a Custom menu.

5. The method of claim 4 wherein (c) comprises copying to the custom menu wherein the custom menu comprises a single page.

6. The method of claim 4 wherein (b) comprises selecting imaging parameters comprising beamforming parameters.

7. The method of claim 4 wherein (b) comprises selecting imaging parameters comprising image processing parameters.

8. The method of claim 4 wherein (b) comprises selecting imaging parameters comprising filtering parameters.

9. The method of claim 4 wherein (b) comprises selecting imaging parameters comprising at least two from the group of: beamforming parameters, image processing parameters and display objects.

10. The method of claim 4 wherein (b) comprises selecting the first imaging parameter comprising a modifiable imaging parameter.

11. The method of claim 4 further comprising:
(d) storing the custom menu after (c).

12. The method of claim 11 further comprising:
(d) repeating (b) and (c) for a different custom menu; and
(e) storing the different custom menu after (d) associated with a different name.

13. The method of claim 4 further comprising:
(d) providing a selection tool;
wherein (b) comprises selecting with the selection tool.

14. The method of claim 13 wherein (d) comprises displaying selection buttons associated with imaging parameters of the first and second menus and wherein (b) comprises selecting the selection buttons for the first and second imaging parameters.

15. The method of claim 4 further comprising:
(d) displaying the custom menu on a display remote from a display connected with the user interface.

16. A method for a user to create a custom menu in a medical imaging system, the method comprising:
(a) providing at least one menu having both a plurality of objects and a custom page;
(b) selecting by a user with a user input at least two of the plurality of objects; and
(c) providing the at least two of the plurality of objects on the custom page in response to (b), the at least two of the plurality of objects corresponding to different functions of the medical imaging system, the functions comprising ways of operating;
(d) modifying a value of a variable corresponding to the at least one of the plurality of objects, the modification being on the custom page, the variable for the function, the value changing a level of the way of operating for the function but not changing the way of operating; and
(e) imaging with the medical imaging system, the imaging responsive to the value of the variable corresponding to the function of the at least one of the plurality of objects.

17. The method of claim 16 further comprising:
(f) displaying the custom page after (c), the custom page having a first set of objects different than any menu page available on the medical imaging system.

* * * * *